United States Patent
Pigamo et al.

(10) Patent No.: US 9,255,047 B2
(45) Date of Patent: *Feb. 9, 2016

(54) PROCESS FOR THE PREPARATION OF FLUORINATED COMPOUNDS

(75) Inventors: Anne Pigamo, Francheville (FR); Michel Devic, Foy Les Lyon (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 712 days.

This patent is subject to a terminal disclaimer.

(21) Appl. No.: 12/602,707

(22) PCT Filed: Aug. 19, 2009

(86) PCT No.: PCT/FR2009/051600
§ 371 (c)(1),
(2), (4) Date: Apr. 20, 2011

(87) PCT Pub. No.: WO2010/029240
PCT Pub. Date: Mar. 18, 2010

(65) Prior Publication Data
US 2011/0190554 A1    Aug. 4, 2011

(30) Foreign Application Priority Data
Sep. 11, 2008 (FR) ...................... 08 56114

(51) Int. Cl.
*C07C 17/354* (2006.01)
*C07C 17/25* (2006.01)
*C07C 21/18* (2006.01)

(52) U.S. Cl.
CPC ............... *C07C 17/25* (2013.01); *C07C 17/354* (2013.01); *C07C 21/18* (2013.01)

(58) Field of Classification Search
CPC ............................ C07C 17/25; C07C 17/354
USPC ........... 570/155, 156, 157, 226; 585/250, 265
See application file for complete search history.

(56) References Cited

U.S. PATENT DOCUMENTS

| | | | |
|---|---|---|---|
| 4,414,185 A | 11/1983 | Harrison | |
| 5,396,000 A | 3/1995 | Nappa et al. | |
| 5,679,875 A | 10/1997 | Aoyama et al. | |
| 6,124,510 A * | 9/2000 | Elsheikh et al. | 570/156 |
| 6,548,719 B1 | 4/2003 | Nair et al. | |
| 7,674,939 B2 * | 3/2010 | Mukhopadhyay et al. | 570/156 |
| 8,329,964 B2 * | 12/2012 | Devic et al. | 570/156 |
| 8,389,779 B2 * | 3/2013 | Avril et al. | 570/157 |
| 2007/0179324 A1 * | 8/2007 | Van Der Puy et al. | 570/156 |
| 2009/0127496 A1 | 5/2009 | Rao et al. | |
| 2009/0264689 A1 | 10/2009 | Rao et al. | |
| 2010/0121115 A1 | 5/2010 | Rao et al. | |
| 2010/0145111 A1 | 6/2010 | Sharratt et al. | |
| 2010/0185029 A1 | 7/2010 | Elsheikh et al. | |

FOREIGN PATENT DOCUMENTS

| | | |
|---|---|---|
| JP | 53-078999 A | 7/1978 |
| JP | 2004018308 | 1/2004 |
| SU | 0 709 537 | 1/1980 |
| WO | 03/027051 | 4/2003 |
| WO | 2007/056194 | 5/2007 |
| WO | 2007/144665 | 12/2007 |
| WO | 2008/030440 | 3/2008 |
| WO | WO 2008030439 A2 * | 3/2008 |
| WO | 2008/075017 | 6/2008 |
| WO | 2009/003157 | 12/2008 |
| WO | 2009/138764 | 11/2009 |

OTHER PUBLICATIONS

Sianesi, D. et al. Fluoroolefins Note I, cis and trans 1,2,3,3,-pentafluoropropylene, Anali di Chmica, Socieata Chimica Italiana, vol. 55, No. 8-9, Jan. 1965, pp. 850-861 (English partial translation of the section from p. 859 paragraph 3 is provided from STIC (Steven Spar)).*
Sianesi, D. et al. Fluoroolefins Note I, cis and trans 1,2,3,3,-pentafluoropropylene, Anali di Chmica, Socieata Chimica Italiana, vol. 55, No. 8-9, Jan. 1965, pp. 850-861.*
Sianesi, D. et al., Fluoro olefins Note I. cis and trans 1,2,3,3,3-pentafluoropropylene, Annali di Chemica, Societa Chimica Italiana, vol. 55, No. 8-9, Jan. 1965, pp. 850-861.
Office Action dated Apr. 4, 2013 for U.S. Appl. No. 13/384,256.
Final Office Action dated Oct. 31, 2013 for U.S. Appl. No. 13/384,256.
WPI Thompson—XP-002568903—Thompson Scientific, London GB; AN—1980-61936C—LOPATKINA.

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

A subject-matter of the invention is a process for the preparation of 2,3,3,3-tetrafluoro-1-propene which comprises the following stages: (i) hydrogenation of hexafluoropropylene to give 1,1,1,2,3,3-hexafluoropropane; (ii) dehydrofluorination of the 1,1,1,2,3,3-hexafluoropropane obtained in the preceding stage to give 1,2,3,3,3-pentafluoro-1-propene; (iii) hydrogenation of the 1,2,3,3,3-pentafluoro-1-propene obtained in the preceding stage to give 1,1,1,2,3-pentafluoropropane; and (iv) dehydrofluorination of the 1,1,1,2,3-pentafluoropropane obtained in the preceding stage to give 2,3,3,3-tetrafluoro-1-propene. Stages (ii) and (iv) are carried out using a water and potassium hydroxide mixture with the potassium hydroxide representing between 58 and 86% by weight of the mixture and at a temperature of between 110 and 180° C.

11 Claims, No Drawings

US 9,255,047 B2

PROCESS FOR THE PREPARATION OF FLUORINATED COMPOUNDS

FIELD OF THE INVENTION

A subject-matter of the invention is a process for the preparation of fluorinated compounds, namely the fluorinated compound 2,3,3,3-tetrafluoro-1-propene.

TECHNOLOGICAL BACKGROUND

Hydrofluorocarbons (HFCs) and in particular hydrofluoroolefins, such as 2,3,3,3-tetrafluoro-1-propene (HFO-1234yf), are compounds known for their properties of refrigerants and heat-transfer fluids, extinguishers, propellants, foaming agents, blowing agents, gaseous dielectrics, polymerization medium or monomer, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

Several processes for the manufacture of 1234yf are known.

WO2008/002499 describes a process for the production of a mixture of 2,3,3,3-tetrafluoro-1-propene (HFO-1234yf) and 1,3,3,3-tetrafluoro-1-propene (HFO-1234ze) by pyrolysis of 1,1,1,2,3-pentafluoropropane (HFC-245eb).

WO2008/002500 describes a process for production of a mixture of 2,3,3,3-tetrafluoro-1-propene (HFO-1234yf) and 1,3,3,3-tetrafluoro-1-propene (HFO-1234ze) by catalytic conversion of 1,1,1,2,3-pentafluoropropane (HFC-245eb) over a dehydrofluorination catalyst.

These two abovementioned patent applications are thus targeted at the production of a mixture comprising a substantial portion of product HFO-1234ze.

WO2007/056194 describes the preparation of HFO-1234yf by dehydrofluorination of HFC-245eb either with potassium hydroxide, typically an aqueous solution of at most 50% by weight of KOH, or in the gas phase in the presence of a catalyst, in particular a catalyst based on nickel, carbon or a combination of these.

The document Knunyants et al., Journal of the USSR Academy of Sciences, Chemistry Department, "Reactions of Fluoroolefins", report 13, "Catalytic Hydrogenation of Perfluoroolefins", 1960, clearly describes various chemical reactions on fluorinated compounds. This document describes the substantially quantitative hydrogenation of HFP over a catalyst based on palladium supported on alumina, the temperature changing from 20° C. to 50° C. and then being maintained at this value. This document describes the dehydrofluorination of 1,1,1,2,3,3-hexafluoropropane (HFC-236ea) by passing through a suspension of KOH in dibutyl ether, in order to produce 1,2,3,3,3-pentafluoro-1-propene (HFO-1225ye) with a yield of only 60%. This document describes the hydrogenation of 1,2,3,3,3-pentafluoro-1-propene (HFO-1225ye) to give 1,1,1,2,3-pentafluoropropane (HFC-245eb) over a catalyst formed of palladium supported on alumina. During this hydrogenation, a hydrogenolysis reaction also takes place, a significant amount of 1,1,1,2-tetrafluoropropane being produced. This document describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether, with a yield of only 70%. These reactions are described independently of one another even if it is indicated that it is possible to combine them in order to synthesize a range of ethylene, propylene and isobutylene derivatives comprising variable amounts of fluorine.

The document U.S. Pat. No. 5,396,000 describes the preparation of 1,1,1,2,3-pentafluoropropane by catalytic dehydrofluorination of 1,1,1,2,3,3-hexafluoropropane (HFC-236ea) to give 1,2,3,3,3-pentafluoro-1-propene (HFO-1225ye), followed by a hydrogenation in order to produce the desired compound. The dehydrohalogenation of HFC-236ea to give HFO-1225ye is carried out in the gas phase, the reaction product being, in one example, conveyed directly to the following reactor in which the hydrogenation of the compound HFO-1225ye to give the compound HFC-245eb takes place. It is also indicated in this document that the compound HFC-236ea can be obtained by hydrogenation of hexafluoropropylene (HFP).

The document U.S. Pat. No. 5,679,875 describes the preparation of 1,1,1,2,3-pentafluoropropane by catalytic dehydrofluorination of 1,1,1,2,3,3-hexafluoropropane (HFC-236ea) to give 1,2,3,3,3-pentafluoro-1-propene (HFO-1225ye), followed by hydrogenation to produce the desired compound. The reactions are carried out in the gas phase. It is also indicated in this document that the compound HFC-236ea can be obtained by hydrogenation of hexafluoropropylene (HFP).

The document WO 2008/030440 describes the preparation of HFO-1234yf from HFO-1225ye by reacting HFO-1225ye with hydrogen in the presence of a catalyst, in order to give HFC-245eb, and by then reacting the HFC-245eb with a basic aqueous solution in the presence of a phase transfer catalyst and a non-aqueous and non-alcoholic solvent.

The document WO 2008/075017 illustrates the dehydrofluorination reaction of 1,1,1,2,3,3-hexafluoropropane (HFC-236ea) to give 1,1,1,2,3-pentafluoropropene (HFO-1225ye) at 150° C. in the presence of a 50% by weight aqueous KOH solution. In the absence of a phase transfer catalyst, the conversion after 3 and a half hours is 57.8% and the selectivity for HFO-1225ye is 52.4% (Test 1). In the presence of a phase transfer catalyst, this conversion is achieved after only 2.5 hours and the selectivity is virtually unchanged (Test 4). As indicated in Table 2 of this document, it is necessary to use an organic solvent in order to increase the selectivity for HFO-1225ye.

There exists a need for a process for the preparation of 1234yf from a starting material which is easily accessible and which results in the desired product with a high selectivity, preferably a high yield and advantageously a high productive output.

SUMMARY OF THE INVENTION

The invention thus provides a process for the preparation of 2,3,3,3-tetrafluoro-1-propene which comprises the following stages:
(i) hydrogenation of hexafluoropropylene to give 1,1,1,2,3,3-hexafluoropropane;
(ii) dehydrofluorination of the 1,1,1,2,3,3-hexafluoropropane obtained in the preceding stage to give 1,2,3,3,3-pentafluoro-1-propene using a water and potassium hydroxide mixture with the potassium hydroxide representing between 58 and 86% by weight of the mixture and at a temperature of between 110 and 180° C.;
(iii) hydrogenation of the 1,2,3,3,3-pentafluoro-1-propene obtained in the preceding stage to give 1,1,1,2,3-pentafluoropropane;
(iv) dehydrofluorination of the 1,1,1,2,3-pentafluoropropane obtained in the preceding stage to give 2,3,3,3- tetrafluoro-1-propene using a water and potassium hydroxide mixture with the potassium hydroxide representing between 58 and 86% by weight of the mixture and at a temperature of between 110 and 180° C.

According to embodiments:

the hydrogenation stages (i) and (iii) are carried out in the same reactor, preferably with the same catalyst, a separation stage optionally being present;

the hydrogenation stages (i) and/or (iii) are carried out in a multistage reactor or in at least two reactors in series, a separation stage optionally being present;

the dehydrofluorination stages (ii) and/or (iv) are carried out in at least two reactors in series, the separation stage optionally being present;

the stream from stage (i) comprising the 1,1,1,2,3,3-hexafluoropropane is conveyed directly to stage (ii) without separation of the reactants;

the stream from stage (i) comprising the 1,1,1,2,3,3-hexafluoropropane is conveyed to stage (ii) after separation of the unreacted reactants, which are optionally recycled to stage (i);

the stream from stage (ii) comprising the 1,2,3,3,3-pentafluoro-1-propene is conveyed to stage (iii) after a purification stage;

the stream from stage (iii) comprising the 1,1,1,2,3-pentafluoropropane is conveyed directly to stage (iv) without separation of the reactants;

the stream from stage (iii) comprising the 1,1,1,2,3-pentafluoropropane is conveyed to stage (iv) after separation of the unreacted reactants, which are optionally recycled to stage (iii).

DETAILED DESCRIPTION OF EMBODIMENTS

The invention uses four reactions in series, the reaction products being conveyed to the following stage, optionally after having been subjected to a treatment, for example a separation treatment, if need be.

It is possible to provide for feeding the following stage in part with reactants not originating from the preceding stage.

In the process, the reaction stages are carried out batchwise, semi-continuously or continuously. Advantageously, the process according to the present invention is carried out continuously. An economical process for the preparation of the compound HFO-1234yf is thus obtained, the starting material HFP being easily available commercially at a low cost.

The hydrogenation stages are carried out conventionally for a person skilled in the art. A person skilled in the art can choose the operating conditions in order for the reactions to be substantially quantitative.

The catalysts capable of being used in these reactions are those known for this purpose. Mention may in particular be made of catalysts based on a metal from Group VIII or rhenium. This catalyst may be supported, for example on carbon, silicon carbide, alumina, aluminium fluoride and the like, or may not be supported, such as Raney nickel. Use may be made, as metal, of platinum or palladium, in particular palladium, advantageously supported on carbon or alumina. It is also possible to combine this metal with another metal, such as silver, copper, gold, tellurium, zinc, chromium, molybdenum and thallium. These hydrogenation catalysts are known.

The catalyst can be present in any appropriate form, for example in the form of a fixed or fluidized bed, preferably as fixed bed. The stream direction can be from the top downwards or from the bottom upwards. The catalyst bed can also comprise a specific distribution of the catalyst in order to manage the flow of heat generated by the exothermic reaction. Thus, it is possible to provide gradients in density of loading, in porosity, and the like, of the catalyst in order to regulate the exothermicity of the reaction. For example, it is possible to provide for the first part of the bed to comprise less catalyst, while the second part comprises more thereof.

It is also possible to provide stages for regeneration of the catalyst in a known way.

It is also possible to provide for the use of a diluting gas, such as nitrogen, helium or argon.

The hydrogenation stages are exothermic. The reaction temperature can be controlled using means positioned for this purpose in the reactor, if need be. The temperature can vary by a few tens of degrees during the reaction, the reaction (i) being more exothermic than the reaction (iii). For example, the inlet temperature can vary from 20° C. to 120° C., preferably between 50 and 100° C., and the increase in temperature can vary from 5° C. to 100° C.

The contact time (ratio of the catalyst volume to the total stream of the charge) is generally between 0.1 and 100 seconds, preferably between 1 and 50 seconds and advantageously between 2 and 10 seconds.

The amount of hydrogen injected can vary within wide limits. The $H_2$/charge ratio can vary within wide limits, in particular between 1 (the stoichiometric amount) and 30, in particular between 1.5 and 20, advantageously between 1.1 and 3. A high ratio will result in a dilution and thus in better management of the exothermicity of the reaction.

The stream resulting from the hydrogenation stages (i) and/or (iii) can be conveyed directly to the following dehydrofluorination stage or can be subjected to a separation stage in order to separate the unreacted reactants (hydrogen, HFP or HFO-1225ye) before being conveyed to the following dehydrofluorination stage. After separation, the unreacted reactants can be recycled.

Preferably, the stream resulting from the hydrogenation stages (i) and/or (iii) is or are conveyed directly to the following dehydrofluorination stage.

The hydrogenation reactions of stage (i) and/or (iii) are preferably substantially quantitative. They can be carried out in a multistage reactor or in at least two reactors in series, a separation stage optionally being present.

The dehydrofluorination reactions are carried out by reacting HFC-236ea and/or HFC-245eb with a water and potassium hydroxide (KOH) mixture in which the potassium hydroxide is present at between 58 and 86% by weight at a temperature of between 110 and 180° C., preferably of greater than 150° C. and advantageously of between 152 and 165° C.

Preferably, the potassium hydroxide is present at between 60 and 75% in weight in the water-KOH mixture.

The water and KOH mixture used can originate from hydrates of formula $KOH.xH_2O$ (x being between 1 and 2). Preferably, the dehydrofluorination reactions are carried out in the presence of these potassium hydroxide hydrates in the molten state and advantageously in the absence of solvent and/or of phase transfer catalyst.

The 1,1,1,2,3,3-hexafluoropropane in stage (ii) and/or the 1,1,1,2,3-pentafluoropropane in stage (iv) is or are converted generally to more than 90%, preferably to more than 95% and advantageously to more than 98%.

A diluting gas (nitrogen, helium, argon or hydrogen) can be used in the dehydrofluorination reaction.

The dehydrofluorination reaction can be carried out in any type of reactor known to a person skilled in the art. Use may be made of a stirred reactor, a static mixer or a reactive column or the HFC-236ea and/or the HFC-245eb can very simply be sparged into the water and KOH mixture in a vessel. Use may also be made of at least two reactors in series.

The amount of KOH involved in the dehydrofluorination reactions, when they are carried out batchwise or semi-continuously, is such that the KOH/HFC-245eb or HFC-236ea molar ratio is between 1 and 20.

During the dehydrofluorination reactions, potassium fluoride is formed and, for reactions carried out continuously, it is preferable to remove from the reaction medium, continuously or batchwise, all or a portion of the KF formed. The potassium fluoride can be separated from the reaction medium by filtration.

During the dehydrofluorination reactions, water is formed and can also be removed continuously or batchwise so as to maintain the KOH content in the water-KOH mixture within the interval described above. Removal of water can be carried out by evaporation.

The stream resulting from the dehydrofluorination stage (ii) comprising the HFO-1225ye can be conveyed directly to stage (iii). Preferably, this stream is purified beforehand, for example by distillation.

The stream resulting from the dehydrofluorination stage (iv) comprising the HFO-1234yf, optionally separated from the HFC-245eb, is subjected to a stage of purification, for example by distillation.

It is possible, in the process, to provide for the hydrogenation stages (i) and (iii) to be carried out in the same reactor, preferably with the same catalyst.

The cohydrogenation is carried out in a first reactor, the outlet stream of which comprises HFC-236ea and HFC-245eb. The outlet stream can be separated and the HFC-236ea is conveyed to a first dehydrofluorination reactor while the HFC-245eb is conveyed to a second dehydrofluorination reactor. The outlet stream from the first dehydrofluorination reactor predominantly comprises HFO-1225ye and optionally unreacted HFC-236ea. The outlet stream from the first dehydrofluorination reactor can be conveyed back to the hydrogenation reactor, thus producing the compound HFC-245eb from this HFO-1225ye. The HFC-236ea possibly separated can be recycled to the top of this dehydrofluorination reactor.

The pressure in the various reactions can be atmospheric or lower than or greater than this atmospheric pressure. The pressure can vary from one reaction to another, if appropriate.

Feeding with reactants generally takes place continuously or can be sequenced, if appropriate.

The reactions are carried out in one or more reactors dedicated to reactions involving halogens. Such reactors are known to a person skilled in the art and can comprise internal coatings based, for example, on Hastelloy®, Inconel®, Monel® or fluoropolymers. The reactor can also comprise heat exchange means, if necessary.

It should be remembered that:
the degree of conversion is the % of the starting material which has reacted (number of moles of starting material which have reacted/number of moles of starting material introduced);
the selectivity for desired product is the ratio of the number of moles of desired product formed to the number of moles of starting material which have reacted;
the yield of desired product is the ratio of the number of moles of desired product formed to the number of moles of starting material introduced, it being possible for the yield of desired product also to be defined as the product of the conversion and of the selectivity;
the contact time is the inverse of the space velocity WHSV;
the space velocity is the ratio of the flow rate by volume of the total gas stream to the volume of the catalytic bed, under standard temperature and pressure conditions.

EXAMPLES

The following examples illustrate the invention without limiting it.

Example 1

Hydrogenation of HFP to Give HFC-236ea

Use is made of a jacketed tubular reactor with an internal diameter of 21 mm and a length of 1.2 m, with circulation of water maintained at 40° C. The reactor is charged with three catalytic beds of the type comprising pellets of Pd supported on alumina. The three catalytic beds differ in the content of the supported Pd and are arranged in increasing concentration. The catalytic bed having the lowest Pd content is found closest to the inlet for the reactants.

Thus, the reactor comprises a bed of 15 cm composed of catalyst having a content of Pd of 0.5% by weight on alumina but diluted with 5 times the volume of silicon carbide, a bed of 10 cm composed of catalyst having a content of Pd of 0.5% by weight on undiluted alumina and a bed of 20 cm of catalyst having a content of Pd of 2.2% by weight on alumina.

Before charging the three catalytic beds, approximately 130 $cm^3$ of corundum (i.e. 37 cm) were introduced into the reactor. 80 $cm^3$ of corundum (25 cm) were also introduced above the first catalytic bed.

The catalyst is activated using a stream of approximately 20 l/h of hydrogen at 250° C. for 12 h before it is first brought into service.

The pressure is 1 bar absolute.

With an HFP flow rate of 150 g/h (1 mol/h) and a hydrogen flow rate of 33.6 Sl/h (1.5 mol/h) and with complete conversion of HFP, a yield of HFC-236ea of 95.2% is obtained.

During the reaction, a maximum temperature of 105° C. was observed for the most dilute catalytic bed and a maximum temperature of 140° C. was observed for the other two catalytic beds.

Example 2

Dehydrofluorination of HFC-236ea to Give HFO-1225ye

Use is made of two vessels with a volume of 1 litre connected in series (the gas stream resulting from the first vessel is used to feed the second vessel) and 1000 g of water and KOH mixture in which the KOH is present at 80% by weight are charged to each vessel. The temperature of the mixture is maintained between 155 and 170° C. 165 g/h of HFC-236ea are continuously introduced for 6 hours. For complete conversion of HFC-236ea, a yield of HFO-1225ye of 93.9% is obtained.

Example 3

Hydrogenation of HFO-1225ye to Give HFC-245eb

Use is made of the same reactor as in Example 1 but with a catalytic charge comprising a bed of 23.5 cm of catalyst comprising 0.2% by weight of Pd on silicon carbide (SiC), a bed of 15 cm of catalyst comprising 0.5% by weight of Pd supported on charcoal and a bed of 40 cm of catalyst comprising 2.0% by weight of Pd on charcoal. The temperature of the water in the jacket is maintained at approximately 85° C. The pressure is 1 bar absolute.

For an HFO-1225ye flow rate of 128 g/h and a hydrogen flow rate of 33.6 Sl/h and with complete conversion, a yield of HFC-245eb of 84% is obtained.

Example 4

Dehydrofluorination of HFC-245eb to Give HFO-1234yf

Use is made of a vessel with a volume of 1 litre comprising 1000 g of a water and KOH mixture in which the KOH is present at 75% by weight. HFC-245eb is introduced continuously into the mixture, maintained at 160° C., for 2 hours with a flow rate of 138 g/h and a conversion of HFC-245eb of 83% is obtained for a selectivity for HFO-1234yf of 100%. The pressure is 1 bar.

Example 5

Use is made of the device of Example 3 with the same catalytic composition, except that the stream at the outlet of the hydrogenation reactor is introduced directly into the water and KOH mixture of the device of Example 2 comprising, in the first reactor, 850 g of water and KOH mixture in which the KOH is present at 80% by weight and, in the second reactor, 637 g of the same mixture.

2.79 mol/h of hydrogen and 1.04 mol/h of HFP are introduced continuously into the hydrogenation reactor for 5.1 hours and, after passing into the reactors comprising the water and KOH mixture, complete conversion of HFP and a yield of HFO-1225ye of 92% are obtained.

Example 6

Use is made of the same device as in Example 5, except that one mol/h of unpurified HFO-1225ye obtained in Example 5 and 1.5 mol/h of hydrogen are introduced continuously for 6.4 hours. For a conversion of HFO-1225ye of 98%, a yield of HFO-1234yf of 96.8% is obtained.

The invention claimed is:

1. Process for the preparation of 2,3,3,3-tetrafluoro-1-propene which comprises the following stages:
   (i) hydrogenation of hexafluoropropylene to give 1,1,1,2,3,3-hexafluoropropane;
   (ii) dehydrofluorination of the 1,1,1,2,3,3-hexafluoropropane obtained in the preceding stage to give 1,2,3,3,3-pentafluoro-1-propene using a water and potassium hydroxide mixture with the potassium hydroxide representing between 58 and 86% by weight of the mixture and at a temperature of between 110 and 180° C.;
   (iii) hydrogenation of the 1,2,3,3,3-pentafluoro-1-propene obtained in the preceding stage to give 1,1,1,2,3-pentafluoropropane;
   (iv) dehydrofluorination of the 1,1,1,2,3-pentafluoropropane obtained in the preceding stage to give 2,3,3,3-tetrafluoro-1-propene using a water and potassium hydroxide mixture with the potassium hydroxide representing between 58 and 86% by weight of the mixture and at a temperature of between 155 and 170° C.

2. The process according to claim 1, in which the potassium hydroxide represents between 60 and 75% by weight of the water-potassium hydroxide mixture of stage (ii) and/or (iv).

3. The process according to claim 1, characterized in that the stream resulting from stage (i) and/or stage (iii) is conveyed directly to the following stage.

4. The process according to claim 1, characterized in that the stream resulting from stage (ii) is subjected to a purification stage before being conveyed to stage (iii).

5. The process according to claim 1, characterized in that it is carried out continuously.

6. The process according to claim 1, characterized in that stage (ii) and/or stage (iv) is carried out in at least two reactors in series.

7. The process according to claim 1, characterized in that stage (i) and/or stage (iii) is carried out in a multistage reactor or in at least two reactors in series.

8. The process according to claim 1 in which stage (ii) and/or stage (iv) is carried out at a temperature of between 155 and 165° C.

9. The process according to claim 1, wherein dehydrofluorination in stage (ii) and/or stage (iv) takes place in the absence of a solvent and/or a phase transfer catalyst.

10. The process according to claim 9, wherein conversion in stage (ii) or stage (iv) is 95% or greater.

11. The process according to claim 9, wherein conversion in stage (ii) and stage (iv) is 95% or greater.

* * * * *